United States Patent
Park et al.

(10) Patent No.: US 10,966,673 B2
(45) Date of Patent: Apr. 6, 2021

(54) X-RAY IMAGING DEVICE, X-RAY DETECTOR, AND X-RAY IMAGING SYSTEM

(71) Applicant: SAMSUNG ELECTRONICS CO., LTD., Suwon-si (KR)

(72) Inventors: Jongseo Park, Yongin-Si (KR); Sungnam Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/638,818

(22) PCT Filed: Aug. 16, 2018

(86) PCT No.: PCT/KR2018/009377
§ 371 (c)(1),
(2) Date: Feb. 13, 2020

(87) PCT Pub. No.: WO2019/074201
PCT Pub. Date: Apr. 18, 2019

(65) Prior Publication Data
US 2020/0187892 A1 Jun. 18, 2020

(30) Foreign Application Priority Data
Oct. 11, 2017 (KR) .......................... 10-2017-0131644

(51) Int. Cl.
*A61B 6/00* (2006.01)
(52) U.S. Cl.
CPC .......... *A61B 6/4494* (2013.01); *A61B 6/4208* (2013.01); *A61B 6/4283* (2013.01);
(Continued)
(58) Field of Classification Search
None
See application file for complete search history.

(56) References Cited

U.S. PATENT DOCUMENTS

| 7,154,994 B2 * | 12/2006 | Gray ................... A61B 6/4233 378/116 |
| 7,983,392 B2 * | 7/2011 | Venturino ............... A61B 6/54 378/98.8 |

(Continued)

FOREIGN PATENT DOCUMENTS

| EP | 2870916 A1 | 5/2015 |
| EP | 2878267 A1 | 6/2015 |

(Continued)

OTHER PUBLICATIONS

International Search Report (PCT/ISA/210) dated Nov. 11, 2018 issued by the International Searching Authority in International Application No. PCT/KR2018/009377.

(Continued)

*Primary Examiner* — Thomas R Artman
(74) *Attorney, Agent, or Firm* — Sughrue Mion, PLLC

(57) ABSTRACT

Provided are an X-ray imaging apparatus, an X-ray detector, and an X-ray imaging system. The X-ray imaging apparatus includes: an X-ray radiation device configured to emit X-rays; a receptor into which a first X-ray detector configured to detect the emitted X-rays is inserted; an X-ray detector sensing interface configured to detect whether the first X-ray detector has been inserted into the receptor, acquire first identification information of the first X-ray detector inserted into the receptor, and generate first position information indicating that the first X-ray detector has been inserted into the receptor; an output interface configured to output information about the first X-ray detector; and a controller configured to control the output interface to output the first position information and the first identification information, wherein the first identification information is identification information set by a workstation of an X-ray imaging system including the X-ray imaging apparatus.

13 Claims, 12 Drawing Sheets

(52) U.S. Cl.
CPC .......... *A61B 6/4405* (2013.01); *A61B 6/4429* (2013.01); *A61B 6/465* (2013.01); *A61B 6/547* (2013.01)

(56) References Cited

U.S. PATENT DOCUMENTS

| | | | | |
|---|---|---|---|---|
| 8,243,883 | B2* | 8/2012 | Omernick | G16H 40/67 378/116 |
| 8,611,501 | B2* | 12/2013 | Kobayashi | G01T 1/17 378/115 |
| 8,744,043 | B2* | 6/2014 | Ohta | A61B 6/06 378/62 |
| 9,405,183 | B2* | 8/2016 | Ando | A61B 6/465 |
| 10,058,297 | B2* | 8/2018 | Park | A61B 6/4283 |
| 10,139,722 | B2* | 11/2018 | Ando | A61B 6/4283 |
| 2006/0109958 | A1 | 5/2006 | Ertel et al. | |
| 2009/0257564 | A1 | 10/2009 | Kito et al. | |
| 2011/0051902 | A1 | 3/2011 | Liu et al. | |
| 2011/0164724 | A1* | 7/2011 | Ohta | A61B 6/563 378/62 |
| 2011/0274251 | A1 | 11/2011 | Omernick et al. | |
| 2015/0131782 | A1* | 5/2015 | Park | A61B 6/4411 378/62 |
| 2017/0143293 | A1* | 5/2017 | Park | H04W 4/80 |
| 2018/0317871 | A1 | 11/2018 | Park et al. | |
| 2019/0313997 | A1 | 10/2019 | Park et al. | |
| 2020/0187892 | A1* | 6/2020 | Park | A61B 6/4283 |

FOREIGN PATENT DOCUMENTS

| | | |
|---|---|---|
| KR | 10-2015-0053708 A | 5/2015 |
| KR | 10-2017-0059883 A | 5/2017 |
| WO | 2015069046 A1 | 5/2015 |

OTHER PUBLICATIONS

Written Opinion (PCT/ISA/237) dated Nov. 11, 2018 issued by the International Searching Authority in International Application No. PCT/KR2018/009377.
Communication dated Jul. 22, 2020, from the European Patent Office in counterpart European Application No. 18866813.1.

* cited by examiner

X-RAY IMAGING DEVICE, X-RAY DETECTOR, AND X-RAY IMAGING SYSTEM

TECHNICAL FIELD

The disclosure relates to X-ray imaging apparatuses, X-ray detectors, and X-ray imaging systems including the X-ray imaging apparatuses and the X-ray detectors.

BACKGROUND ART

X-rays are electromagnetic waves having wavelengths of 0.01 to 100 angstroms (Å) and, due to their ability to be transmitted through objects, may be widely used in medical apparatuses for imaging the inside of a living body or in non-destructive testing equipment for industrial use.

A basic principle of an X-ray imaging apparatus is that an internal structure of an object is examined by transmitting X-rays emitted from an X-ray tube (or X-ray source) through an object and detecting a difference in intensities of the transmitted X-rays via an X-ray detector. The X-ray imaging apparatus facilitates observation of an internal structure of an object by using a principle in which penetrating power of an X-ray varies depending on the density of the object and atomic numbers of atoms constituting the object. As a wavelength of an X-ray decreases, penetrating power of the X-ray increases and a captured image becomes brighter.

An X-ray imaging apparatus includes an X-ray tube (or X-ray source) for generating X-rays and emitting the generated X-rays toward an object and an X-ray detector for detecting X-rays that have passed through the object. To image various parts of the object, the X-ray tube (or X-ray source) may be movably mounted, and the X-ray detector may be installed in an imaging table or stand or be provided as a portable detector.

In the related art, X-ray detectors are distinguished from one another by their identification marks such as numbers displayed on outer surfaces thereof. However, according to the related art, when an X-ray detector is inserted into a receptor (e.g., a bucky) of an X-ray imaging apparatus, the X-ray detector cannot be identified by its physical mark thereon since the physical mark is invisible from outside. In other words, a user is inconvenienced in having to remove the X-ray detector from the receptor for identification.

DESCRIPTION OF EMBODIMENTS

Technical Problem

Provided are medical imaging apparatuses configured to detect information about an X-ray detector inserted into a receptor and display the detected information.

The technical problems of the present disclosure are not limited to the aforementioned technical features, and other unstated technical problems may be inferred from embodiments below.

Solution to Problem

In accordance with an aspect of the disclosure, an X-ray imaging apparatus includes: an X-ray radiation device configured to emit X-rays; a receptor into which a first X-ray detector configured to detect the emitted X-rays is inserted; an X-ray detector sensing interface configured to detect whether the first X-ray detector has been inserted into the receptor, acquire first identification (ID) information of the first X-ray detector inserted into the receptor, and generate first position information indicating that the first X-ray detector has been inserted into the receptor; an output interface configured to output information about the first X-ray detector; and a controller configured to control the output interface to output the first position information and the first ID information, wherein the first ID information is ID information set by a workstation of an X-ray imaging system including the X-ray imaging apparatus.

The first X-ray detector is further configured to output an optical signal corresponding to the first identification information, wherein the X-ray detector sensing interface includes an optical sensor configured to detect the optical signal, and wherein the controller is further configured to acquire the first identification information based on the detected optical signal.

The controller is further configured to acquire the first identification information corresponding to a color of the optical signal and control the output interface to output the acquired first identification information as information about the color of the optical signal.

The first X-ray detector includes a plurality of light sources configured to respectively output optical signals, wherein the optical sensor is further configured to detect the number of light sources from which optical signals are output from among the plurality of light sources in the first X-ray detector, and wherein the controller is further configured to acquire information about a remaining battery capacity of the first X-ray detector based on the detected number of light sources and control the output interface to further output the information about the remaining battery capacity of the first X-ray detector.

The output interface includes a communication interface configured to transmit the first identification information to a mobile device comprising a display.

The X-ray detector sensing interface is further configured to acquire information about a status of the first X-ray detector via short-range communication, and wherein the controller is further configured to control the output interface to output the information about the status of the first X-ray detector.

An X-ray imaging system includes a plurality of X-ray imaging apparatuses, each of which is the X-ray imaging apparatus of claim 1; and a workstation configured to control operations of the plurality of X-ray imaging apparatuses, wherein each of the plurality of X-ray imaging apparatus is configured to acquire first identification information of the first X-ray detector when the first X-ray detector is inserted into the receptor of the X-ray imaging apparatus and generate first position information indicating that the first X-ray detector has been inserted into the receptor, and transmit the first identification information and the first position information to the workstation, and wherein the workstation is configured to control the first X-ray detector to be activated based on the first identification information and the first position information and control the X-ray radiation device to emit X-rays toward the activated first X-ray detector.

The X-ray imaging apparatus is further configured to detect an optical signal output from the first X-ray detector and acquire, based on the detected optical signal, the first identification information corresponding to the optical signal.

The X-ray imaging apparatus is further configured to acquire the first identification information corresponding to a color of the optical signal.

The workstation is further configured to set different pieces of identification information respectively with respect to a plurality of X-ray detectors, wherein the different pieces of identification information respectively correspond to different colors, and wherein each of the plurality of X-ray detectors is configured to output an optical signal of a color corresponding to identification information of a corresponding X-ray detector.

In accordance with another aspect of the disclosure, a method of controlling an X-ray imaging apparatus includes: detecting whether a first X-ray detector has been inserted into a receptor; acquiring first ID information of the first X-ray detector inserted into the receptor from the first X-ray detector; generating first position information indicating that the first X-ray detector has been inserted into the receptor; and outputting the first position information and the first ID information, wherein the first ID information is ID information set by a workstation of an X-ray imaging system including the X-ray imaging apparatus.

The detecting of the first X-ray detector includes outputting an optical signal corresponding to the first identification information generated by an output interface of the first X-ray detector, and wherein the acquiring of the first identification information includes acquiring the first identification information based on the detected optical signal.

The acquiring of the first identification information includes acquiring the first identification information corresponding to a color of the optical signal, and wherein the outputting of the first identification information includes outputting the first identification information as information about the color of the optical signal.

The detecting of the first X-ray detector includes detecting the number of light sources from which optical signals are output, from among a plurality of light sources included in the first X-ray detector and configured to respectively output optical signals, wherein the acquiring of the first identification information includes acquiring information about a remaining battery capacity of the first X-ray detector based on the detected number of light sources, and wherein the outputting of the first identification information includes outputting the information about the remaining battery capacity of the first X-ray detector.

The method may further include transmitting the first identification information to a mobile device.

The acquiring of the first identification information includes acquiring information about a status of the first X-ray detector from the first X-ray detector, and wherein the outputting of the first identification information includes outputting the information about the status of the first X-ray detector.

The method may further include transmitting, to the workstation, the first identification information and the first position information indicating that the first X-ray detector has been inserted into the receptor of the X-ray imaging apparatus, wherein the transmitting is performed by the X-ray imaging apparatus, controlling the first X-ray detector to be activated based on the first identification information and the first position information, wherein the controlling is performed by the workstation, and controlling X-rays to be emitted toward the activated first X-ray detector, wherein the controlling is performed by the workstation.

The method may further include setting different pieces of identification information respectively with respect to a plurality of X-ray detectors, wherein the setting is performed by the workstation and outputting an optical signal of a color corresponding to identification information of the first X-ray detector, wherein the outputting is performed by the first X-ray detector.

In accordance with another aspect of the disclosure, a computer program product includes a computer-readable storage medium having stored therein instructions to: detect whether a first X-ray detector has been inserted into a receptor; acquire first ID information of the first X-ray detector inserted into the receptor from the first X-ray detector; generate first position information indicating that the first X-ray detector has been inserted into the receptor; and output the first position information and the first ID information, wherein the first ID information is ID information set by a workstation of an X-ray imaging system including the X-ray imaging apparatus.

MODE OF DISCLOSURE

Figure 1:
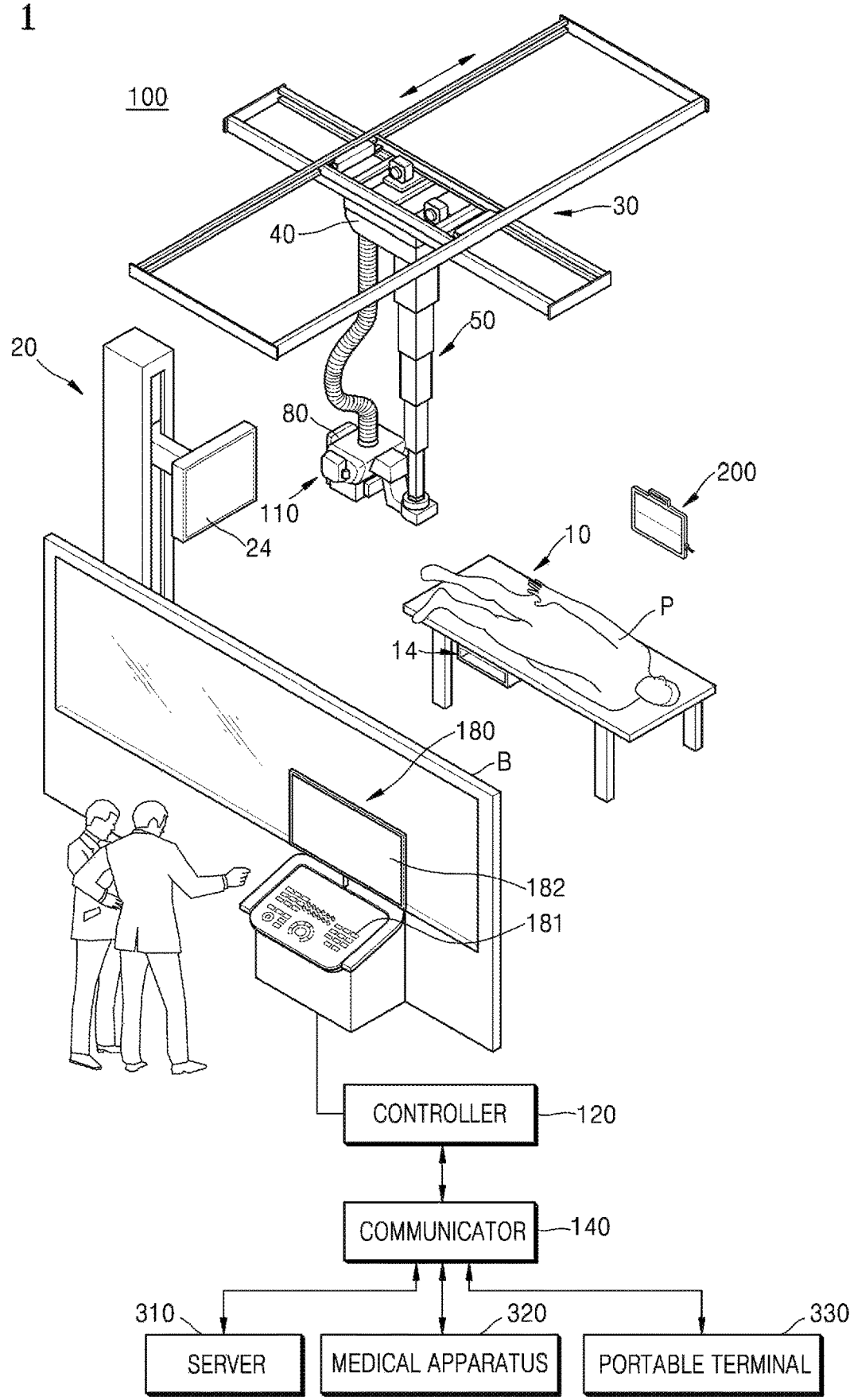
FIG. 1 is an external view and block diagram of a configuration of an X-ray imaging apparatus according to an embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In the present specification, an image may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and may include a human, an animal, or a part of a human or animal. For example, the object may include a body part (an organ, tissue, etc.) or a phantom.

FIG. 1 is an external view and block diagram of a configuration of an X-ray imaging apparatus 100 according to an embodiment. In FIG. 1, it is assumed that the X-ray imaging apparatus 100 is a fixed X-ray apparatus.

Referring to FIG. 1, the X-ray imaging apparatus 100 includes an X-ray radiation device for generating and emitting X-rays, an X-ray detector 200 for detecting X-rays that are emitted by the X-ray radiation device 110 and transmitted through an object P, and a workstation 180 for receiving a command from a user and providing information to the user. The X-ray imaging apparatus 100 may further include a controller 120 for controlling the X-ray imaging apparatus 100 according to the received command, and a communication interface 140 for communicating with an external device.

All or some components of the controller 120 and the communication interface 140 may be included in the workstation 180 or be separate from the workstation 180.

The X-ray radiation device 110 may include an X-ray source for generating X-rays and a collimator for adjusting a region irradiated with the X-rays generated by the X-ray source.

A guide rail 30 may be provided on a ceiling of an examination room in which the X-ray imaging apparatus 100 is located, and the X-ray radiation device 110 may be coupled to a moving carriage 40 that is movable along the guide rail 30 such that the X-ray radiation device 110 may be moved to a position corresponding to the object P. The moving carriage 40 and the X-ray radiation device 110 may be connected to each other via a foldable post frame 50 such that a height of the X-ray radiation device 110 may be adjusted.

The workstation 180 may include an input device 181 for receiving a user command and a display 182 for displaying information.

The input device 181 may receive commands for controlling imaging protocols, imaging conditions, imaging timing, and locations of the X-ray radiation device 110. The input device 181 may include a keyboard, a mouse, a touch screen, a microphone, a voice recognizer, etc.

The display 182 may display a screen for guiding a user's input, an X-ray image, a screen for displaying a state of the X-ray imaging apparatus 100, and the like.

The controller 120 may control imaging conditions and imaging timing of the X-ray radiation device 110 according to a command input by the user and may generate a medical image based on image data received from an X-ray detector 200. Furthermore, the controller 120 may control a position or orientation of the X-ray radiation device 110 or mounting units (e.g., receptors) and 24, each having the X-ray detector 200 mounted therein, according to imaging protocols and a position of the object P.

The controller 120 may include a memory configured to store programs for performing the operations of the X-ray imaging apparatus 100 and a processor or a microprocessor configured to execute the stored programs. The controller 120 may include a single processor or a plurality of processors or microprocessors. When the controller 120 includes the plurality of processors, the plurality of processors may be integrated onto a single chip or be physically separated from one another.

The X-ray imaging apparatus 100 may be connected to external devices such as an external server 310, a medical apparatus 320, and/or a portable terminal 330 (e.g., a mobile device, a smart phone, a tablet PC, or a wearable device) in order to transmit or receive data via the communication interface 140.

The communication interface 140 may include at least one component that enables communication with an external device. For example, the communication interface 140 may include at least one of a local area communication module, a wired communication module, and a wireless communication module.

The communication interface 140 may receive a control signal from an external device and transmit the received control signal to the controller 120 so that the controller 120 may control the X-ray imaging apparatus 100 according to the received control signal.

In addition, by transmitting a control signal to an external device via the communication interface 140, the controller 120 may control the external device according to the control signal. For example, the external device may process data of the external device according to the control signal received from the controller 120 via the communication interface 140.

The communication interface 140 may further include an internal communication module that enables communications between components of the X-ray imaging apparatus 100. A program for controlling the X-ray imaging apparatus 100 may be installed on the external device and may include instructions for performing some or all of the operations of the controller 120.

The program may be preinstalled on the portable terminal 330, or a user of the portable terminal 330 may download the program from a server providing an application for installation. The server that provides applications may include a recording medium where the program is stored.

Furthermore, the X-ray detector 200 may be implemented as a fixed X-ray detector that is fixedly mounted to a stand 20 or a table 10 or as a portable X-ray detector that may be detachably mounted in the mounting unit 14 or 24 or can be used at arbitrary positions. The portable X-ray detector may be implemented as a wired or wireless detector according to a data transmission technique and a power supply method.

The X-ray detector 200 may or may not be a component of the X-ray imaging apparatus 100. When the X-ray detector 200 is not a component of the X-ray imaging apparatus 100, the X-ray detector 200 may be registered by the user with the X-ray imaging apparatus 100. Furthermore, in both cases, the X-ray detector 200 may be connected to the controller 120 via the communication interface 140 to receive a control signal from or transmit image data to the controller 120.

A sub-user interface 80 that provides information to a user and receives a command from the user may be provided on one side of the X-ray radiation device 110. The sub-user interface 80 may also perform some or all of the functions performed by the input device 181 and the display 182 of the workstation 180.

When all or some components of the controller 120 and the communication interface 140 are separate from the workstation 180, they may be included in the sub-user interface 80 provided on the X-ray radiation device 110.

Although FIG. 1 shows a fixed X-ray apparatus connected to the ceiling of the examination room, examples of the X-ray imaging apparatus 100 may include a C-arm type X-ray apparatus, a mobile X-ray apparatus, and other X-ray apparatuses having various structures that will be apparent to those of ordinary skill in the art.

Figure 2:
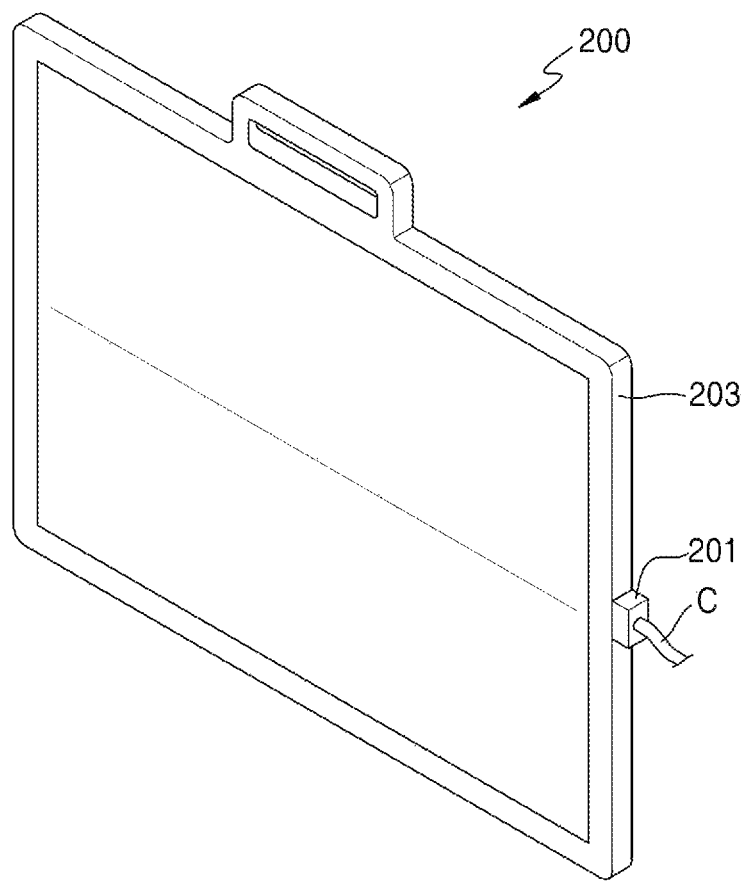
FIG. 2 is an external view of an X-ray detector implemented as a portable X-ray detector, according to an embodiment.

FIG. 2 is an external view of the X-ray detector 200.

As described above, the X-ray detector 200 used in the X-ray imaging apparatus 100 may be implemented as a portable X-ray detector. The X-ray detector 200 may be equipped with a battery for supplying power to operate wirelessly, or as shown in FIG. 2, may operate by connecting a charge port 201 to a separate power supply via a cable C.

A case 203 maintains an external appearance of the X-ray detector 200 and has therein a plurality of detecting elements for detecting X-rays and converting the X-rays into image data, a memory for temporarily or permanently storing the image data, a communication module for receiving a control signal from the X-ray imaging apparatus 100 or transmitting the image data to the X-ray imaging apparatus 100, and a battery. Further, image correction information and intrinsic identification (ID) information of the X-ray detector 200 may be stored in the memory, and the stored ID information may be transmitted together with the image data during communication with the X-ray imaging apparatus 100.

Figure 3:
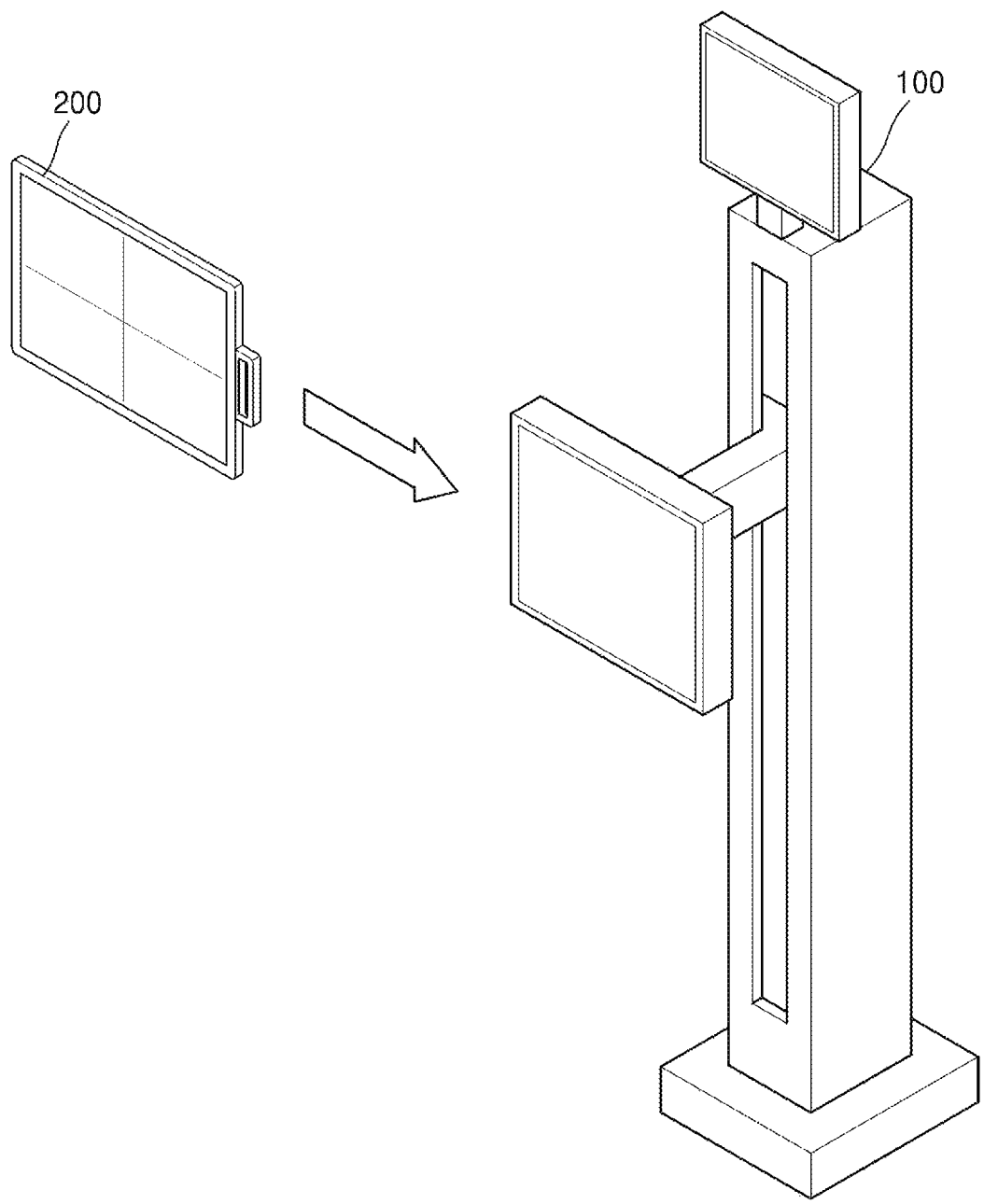
FIG. 3 illustrates an X-ray imaging apparatus and an X-ray detector according to an embodiment.

FIG. 3 illustrates an X-ray imaging apparatus 100 and an X-ray detector 200 according to an embodiment.

According to an embodiment, an X-ray imaging system may include a plurality of X-ray detectors, a plurality of X-ray imaging apparatuses, and the workstation (180 of FIG. 1). The workstation 180 may set different pieces of ID information respectively with respect to the plurality of X-ray detectors.

According to the embodiment shown in FIG. 3, each of the plurality of X-ray imaging apparatuses may detect whether an X-ray detector has been inserted therein. When the X-ray detector 200 that is one of the plurality of X-ray detectors is inserted into a mounting unit (e.g., a receptor) of one of the plurality of X-ray imaging apparatuses, the X-ray imaging apparatus 100 with the X-ray detector 200 inserted therein may acquire ID information from the inserted X-ray detector 200. The X-ray imaging apparatus 100 may also generate position information of the X-ray detector 200. The position information of the X-ray detector 200 may include information indicating the X-ray imaging apparatus 100 with the X-ray detector 200 inserted therein. ID information and position information of the X-ray detector 200 will be described in more detail below with reference to FIGS. 4 through 9.

According to an embodiment, the workstation 180 may receive ID information and position information of the X-ray detector 200 from the X-ray imaging apparatus 100. The workstation 180 may control the X-ray detector 200 to be activated based on the ID information and the position information of the X-ray detector 200. The workstation 180 may also control the X-ray radiation device (110 of FIG. 1) to emit X-rays toward the activated X-ray detector 200. The operation of the workstation 180 will be described in more detail below with reference to FIGS. 10 and 11.

Figure 4:
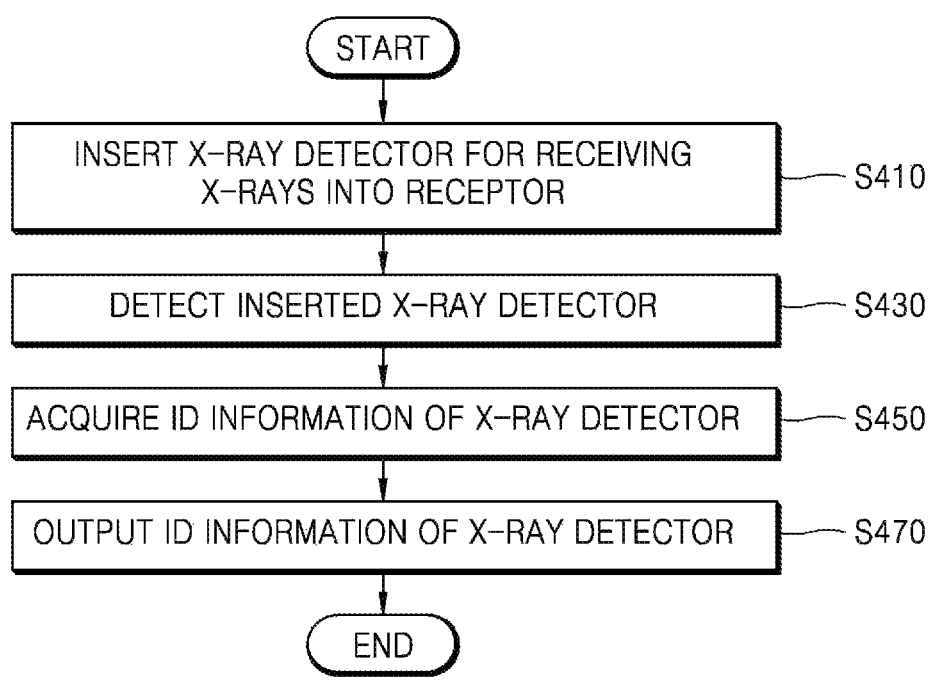
FIG. 4 is a flowchart of a method of detecting identification (ID) information of an X-ray detector and outputting the detected ID information, according to an embodiment.

FIG. 4 is a flowchart of a method of detecting ID information of the X-ray detector 200 and outputting the detected ID information, according to an embodiment.

Referring to FIG. 4, the X-ray detector 200 may be inserted into a mounting unit (e.g., receptor (130 of FIG. 5)) of the X-ray imaging apparatus 100 (S410).

According to an embodiment, ID information of the X-ray detector 200 may be set. The ID information of the X-ray detector 200 may include visual information that may help a user to select an X-ray detector to be used for X-ray imaging. The X-ray detector 200 may include ID information set by the workstation 180 so that the X-ray detector 200 may be distinguished from the other X-ray detectors.

According to an embodiment, the workstation 180 may set different pieces of ID information respectively with respect to the plurality of X-ray detectors for use in the X-ray imaging system. The workstation 180 may set ID information with respect to the X-ray detector 200 based on unique information of the X-ray detector 200.

According to an embodiment, the unique information of the X-ray detector 200 may include a serial number and Internet Protocol (IP) address information of the X-ray detector 200 and other information composed of numerals, letters, or any combination thereof. The serial number of the X-ray detector 200 may include a unique identifier assigned to the X-ray detector 200 during a manufacturing process. Furthermore, the IP address information of the X-ray detector 200 may include an IP address value to be used for communication between the X-ray detector 200 and a predetermined access point (AP).

According to an embodiment, the workstation 180 may register the X-ray detector 200 with the X-ray imaging system. By registering the X-ray detector 200 with the X-ray imaging system, the workstation 180 may allow the registered X-ray detector 200 to communicate with the X-ray imaging apparatus 100 or activate the registered X-ray detector 200.

According to an embodiment, the workstation 180 may set ID information with respect to the X-ray detector 200 when registering the X-ray detector 200 with the X-ray imaging system. For example, the workstation 180 may set ID information that is used to distinguish the X-ray detector 200 from other X-ray detectors when the X-ray detector 200 is registered with the X-ray imaging system by using unique information of the X-ray detector 200. The workstation 180 may set ID information of the X-ray detector 200 based on a user input. Furthermore, the workstation 180 may delete and reset the ID information of the X-ray detector 200 based on a user input.

According to an embodiment, the workstation 180 may transmit the set ID information to the X-ray detector 200. The X-ray detector 200 may then store the set ID information.

According to an embodiment, the ID information of the X-ray detector 200 may include letters, numerals, and symbols. Furthermore, the ID information of the X-ray detector 200 may be a color designated by the workstation 180.

According to an embodiment, the X-ray detector 200 may output its ID information via an output interface (280 of FIG. 6) thereof. For example, the output interface 280 of the X-ray detector 200 may include a light source for outputting an optical signal. The X-ray detector 200 may output an optical signal of a color set by the workstation 180. As another example, the X-ray detector 200 may include a light-emitting diode (LED) display, other light-emitting devices, and a liquid crystal display (LCD) for displaying ID information composed of letters, numerals, or any combination thereof.

The X-ray imaging apparatus 100 may detect the X-ray detector 200 that has been inserted into the receptor 130 (S430).

According to an embodiment, the X-ray imaging apparatus 100 may detect the X-ray detector 200 that has been inserted into the receptor 130 by using a magnetic sensor. For example, the X-ray imaging apparatus 100 and the X-ray detector 200 may each include a magnetic sensor. The X-ray imaging apparatus 100 may detect the X-ray detector 200 based on a strength and a direction of an electric field created when the X-ray detector 200 is inserted into the receptor 130 of the X-ray imaging apparatus 100.

According to an embodiment, the X-ray imaging apparatus 100 may detect the X-ray detector 200 that has been inserted into the receptor 130 by using a short-range communication method such as Near Field Communication (NFC), radio frequency identification (RFID), and Bluetooth. For example, the X-ray imaging apparatus 100 may detect the X-ray detector 200 based on exchange of data generated when the X-ray detector 200 is inserted into the receptor 130.

According to an embodiment, the X-ray imaging apparatus 100 may detect the X-ray detector 200 that has been inserted into the receptor 130, based on ID information output from the X-ray detector 200. For example, the X-ray imaging apparatus 100 may detect the X-ray detector 200 that has been inserted into the receptor 130 by detecting an optical signal generated by a light source of the X-ray detector 200.

The X-ray imaging apparatus 100 may acquire ID information of the X-ray detector 200 inserted into the receptor 130 (S450).

According to an embodiment, the X-ray imaging apparatus 100 may acquire ID information of the X-ray detector 200 by receiving the ID information from the X-ray detector 200 via short-range communication such as NFC, RFID, and Bluetooth. For example, the X-ray imaging apparatus 100 may create a short-range communication network with the X-ray detector 200 when the X-ray detector 200 is inserted into the receptor 130. The X-ray imaging apparatus 100 may receive the ID information of the X-ray detector 200 from the X-ray detector 200 over the created short-range communication network.

According to an embodiment, the X-ray imaging apparatus 100 may acquire the ID information of the X-ray detector 200 based on an optical signal output from the X-ray detector 200. For example, the ID information of the X-ray detector 200 may correspond to a color designated by the workstation 180. The X-ray detector 200 may output a color designated by the workstation 180 as an optical signal. The X-ray imaging apparatus 100 may detect the color of the optical signal output by the X-ray detector 200. The X-ray imaging apparatus 100 may acquire the ID information of the X-ray detector 200, which corresponds to the detected color of the optical signal.

According to an embodiment, when the ID information of the X-ray detector 200 is acquired, the X-ray imaging apparatus 100 may also acquire information about a status of the X-ray detector 200. The information about the status of the X-ray detector 200 may include pieces of information about a remaining battery capacity, an activation state, and communication sensitivity of the X-ray detector 200, information about the number of X-ray images that are to be captured by the X-ray detector 200, and information about whether the X-ray detector 200 is currently transmitting an image to the workstation 180. For example, the X-ray imaging apparatus 100 may acquire information about a status of the X-ray detector 200 from the X-ray detector 200 over a short-range communication network created when the X-ray detector 200 is inserted into the receptor 130.

According to an embodiment, when the ID information of the X-ray detector 200 is acquired, the X-ray imaging apparatus 100 may also acquire information about a remaining battery capacity of the X-ray detector 200 based on an optical signal output from the X-ray detector 200. For example, the X-ray detector 200 may include a plurality of light sources for outputting optical signals. The X-ray imaging apparatus 100 may detect the number of light sources from which optical signals are output, among the plurality of light sources in the X-ray detector 200. The X-ray imaging apparatus 100 may acquire information about a remaining battery capacity of the X-ray detector 200 based on the detected number of light sources, as will be described below with reference to FIG. 12.

According to an embodiment, when the ID information of the X-ray detector 200 is acquired, the X-ray imaging apparatus 100 may generate position information indicating that the X-ray detector 200 has been inserted into the receptor 130 of the X-ray imaging apparatus 100 (hereinafter, referred to as 'position information of the X-ray detector 200') based on the ID information of the X-ray detector 200. For example, the position information of the X-ray detector 200 may include at least one of information indicating that the X-ray detector 200 has been inserted into a receptor of a stand type X-ray imaging apparatus (hereinafter, referred to as 'stand position information'), information indicating that the X-ray detector 200 has been inserted into a receptor of a table type X-ray imaging apparatus (hereinafter, referred to as 'table position information'), and information indicating that the X-ray detector 200 has not fit into any receptor (hereinafter, referred to as 'portable position information'). For example, the X-ray imaging apparatus 100 may acquire a yellow color as ID information of the X-ray detector 200 set to a yellow color and generate position information indicating that the X-ray imaging apparatus 100 is a stand type X-ray imaging apparatus.

The X-ray imaging apparatus 100 may output the ID information of the X-ray detector 200 inserted into the receptor 130 (S470).

Figure 5:
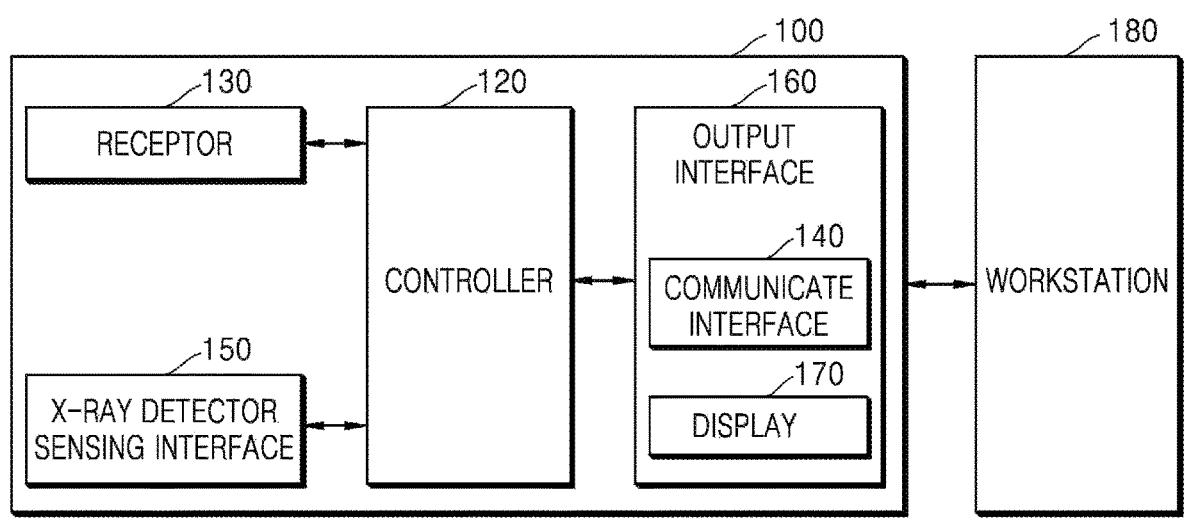
FIG. 5 is a block diagram of a configuration of an X-ray imaging apparatus, according to an embodiment.

According to an embodiment, the X-ray imaging apparatus 100 may include a display (170 of FIG. 5). The X-ray imaging apparatus 100 may display on the display 170 at least one of information about whether the X-ray detector 200 has been inserted into the receptor 130 and ID information and position information of the X-ray detector 200 inserted into the receptor 130.

According to an embodiment, the X-ray imaging apparatus 100 may include a communication interface (140 of FIG. 1). The X-ray imaging apparatus 100 may transmit ID information and position information of the X-ray detector 200 to the workstation 180. By using the communication interface 140, the X-ray imaging apparatus 100 may transmit, to a mobile device (330 of FIG. 8), at least one of information about whether the X-ray detector 200 has been inserted into the receptor 130, ID information, and position information of the X-ray detector 200 inserted into the receptor 130. The mobile device 330 may display the received at least one piece of information on a display included therein. Displaying of information about the X-ray detector 200 will be described in more detail below with reference to FIGS. 7 through 9.

FIG. 5 is a block diagram of a configuration of the X-ray imaging apparatus 100, according to an embodiment.

Referring to FIG. 5, the X-ray imaging apparatus 100 may include a controller 120, the receptor 130, an X-ray detector sensing interface 150, and an output interface 160. Furthermore, the output interface 160 of the X-ray imaging apparatus 100 may include a communication interface 140 and the display 170. However, all of the components shown in FIG. 5 are not essential components of the X-ray imaging apparatus 100. It will be understood by those of ordinary skill in the art that the X-ray imaging apparatus 100 may include more or fewer components than those shown in FIG. 5. For example, the X-ray imaging apparatus 100 may further include a storage (not shown) that stores programs for processing and control by the controller 120 and data that is input to or output from the X-ray imaging apparatus 100.

According to an embodiment, the controller 120 may control all operations of the receptor 130, the communication interface 140, the X-ray detector sensing interface 150, the output interface 160, the display 170, etc. by executing the programs stored in the storage.

According to an embodiment, the controller 120 may acquire ID information and position information of the X-ray detector 200. The controller 120 may acquire the ID information of the X-ray detector 200 based on an optical signal from the X-ray detector 200. In detail, the controller 120 may acquire the ID information of the X-ray detector 200 based on a color of the optical signal. The controller 120 may acquire information about a remaining battery capacity of the X-ray detector 200 based on the number of light sources from which optical signals are output among a plurality of light sources in the X-ray detector 200.

According to an embodiment, the X-ray detector 200 may be inserted into the receptor 130. The receptor 130 may affix the inserted X-ray detector 200 thereto such that the X-ray detector 200 may detect X-rays emitted by the X-ray radiation device (110 of FIG. 1).

According to an embodiment, the X-ray detector sensing interface 150 may detect whether the X-ray detector 200 has been inserted into the receptor 130. For example, the X-ray detector sensing interface 150 may be a magnetic sensor mounted in the receptor 130. As another example, the X-ray detector sensing interface 150 may be an optical sensor located in the receptor 130. As another example, the X-ray detector sensing interface 150 may be a short-range communication interface such as an NFC, RFID, or Bluetooth device. Descriptions are already provided above with respect to the method of detecting whether the X-ray detector 200 has been inserted into the receptor 130, and thus, will not be repeated below.

According to an embodiment, the X-ray detector sensing interface 150 may acquire ID information of the X-ray detector 200. For example, the X-ray detector sensing interface 150 may acquire ID information of the X-ray detector 200 by receiving the ID information of the X-ray detector 200 from the X-ray detector 200 via short-range communication such as NFC, RFID, and Bluetooth. As another example, the X-ray detector sensing interface 150 may detect a color of an optical signal output from the X-ray detector 200 to thereby acquire ID information of the X-ray detector 200 corresponding to the color of the optical signal. Descriptions are already provided above with respect to the method by which the X-ray detector sensing interface 150 acquires ID information of the X-ray detector 200, and thus, will not be repeated below.

According to an embodiment, the X-ray detector sensing interface 150 may generate position information indicating that the X-ray detector 200 has been inserted into the receptor 130. When ID information of the X-ray detector 200 is acquired, the X-ray imaging apparatus 100 may generate, based on the ID information of the X-ray detector 200, position information indicating that the X-ray detector 200 has been inserted into the receptor 130 of the X-ray imaging apparatus 100. For example, the position information of the X-ray detector 200 may include at least one of stand position information, table position information, and portable position information.

According to an embodiment, when the ID information of the X-ray detector 200 is acquired, the X-ray detector sensing interface 150 may also acquire information about a status of the X-ray detector 200. The information about the status of the X-ray detector 200 may include pieces of information about a remaining battery capacity and an activation state of the X-ray detector 200, information about the number of X-ray images that are to be captured by the X-ray detector 200, and information about whether the X-ray detector 200 is currently transmitting an image to the workstation 180. For example, the X-ray imaging apparatus 100 may acquire information about a status of the X-ray detector 200 from the X-ray detector 200 over a short-range communication network created when the X-ray detector 200 is inserted into the receptor 130. As another example, the X-ray imaging apparatus 100 may acquire information about a remaining battery capacity of the X-ray detector 200 based on an optical signal output from the X-ray detector 200. Displaying information about the X-ray detector 200 will be described in more detail below with reference to FIG. 12.

According to an embodiment, the output interface 160 may include the communication interface 140 and the display 170. The output interface 160 may further include an audio output interface (not shown) for outputting an audio signal.

According to an embodiment, the communication interface 140 may communicate with components constituting the X-ray imaging system.

For example, the communication interface 140 may communicate with the X-ray detector 200. In detail, the communication interface 140 may include a module for performing short-range communication such as NFC, RFID, and Bluetooth. The communication interface 140 may receive ID information of the X-ray detector 200 from the X-ray detector via short-range communication such as NFC, RFID, and Bluetooth.

As another example, the communication interface 140 may communicate with the workstation 180. In detail, the communication interface 140 may transmit ID information and position information of the X-ray detector 200 to the workstation 180. Furthermore, the communication interface 140 may receive a control signal for controlling the X-ray imaging apparatus 100 from the workstation 180. In addition, the communication interface 140 may receive a control signal that controls the X-ray detector 200 to be activated from the workstation 180.

According to an embodiment, the communication interface 140 may communicate with an external device (e.g., the mobile device 330). For example, the communication interface 140 may transmit ID information and position information of the X-ray detector 200 to the mobile device 330. As another example, the communication interface 140 may transmit information about a status of the X-ray detector 200 to the mobile device 330. Information about a status of the X-ray detector 200 may include pieces of information about a remaining battery capacity and an activation state of the X-ray detector 200, information about the number of X-ray images that are to be captured by the X-ray detector 200, and information about whether the X-ray detector 200 is currently transmitting an image to the workstation 180.

According to an embodiment, the display 170 may output ID information and position information of the X-ray detector 200 by displaying the same. Furthermore, the display 170 may output information about a status of the X-ray detector 200 by displaying the same. The information about the status of the X-ray detector 200 may include pieces of information about a remaining battery capacity and an activation state of the X-ray detector 200, information about the number of X-ray images that are to be captured by the X-ray detector 200, and information about whether the X-ray detector 200 is currently transmitting an image to the workstation 180.

According to an embodiment, the display 170 may include at least one of an LCD, a thin film transistor-LCD (TFT-LCD), an organic LED (OLED), a flexible display, a three-dimensional (3D) display, and an electrophoretic display.

The workstation 180 may control all operations of the X-ray imaging apparatus 100 and the X-ray detector 200 that constitute the X-ray imaging system. The workstation 180 may set different pieces of ID information respectively with respect to a plurality of X-ray detectors. The workstation 180 may control the X-ray detector 200 to be activated. The workstation 180 may also control the X-ray radiation device 110 to emit X-rays toward the activated X-ray detector 200. An operation of the workstation 180 will be described in more detail below with reference to FIG. 10.

Figure 6:
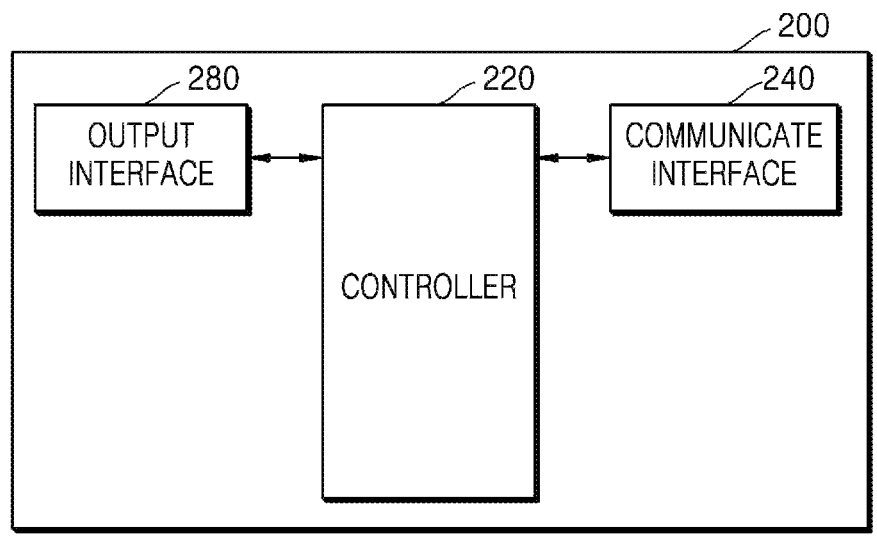
FIG. 6 is a block diagram of a configuration of an X-ray detector according to an embodiment.

FIG. 6 is a block diagram of a configuration of the X-ray detector 200 according to an embodiment.

Referring to FIG. 6, the X-ray detector 200 may include a controller 220, a communication interface 240, and the output interface 280. However, all of the components shown in FIG. 6 are not essential components of the X-ray detector 200. It will be understood by those of ordinary skill in the art that the X-ray detector 200 may include more or fewer components than those shown in FIG. 6. For example, the X-ray detector 200 may further include a storage (not shown) that stores programs for processing and control by the controller 220 and data that is input to or output from the X-ray detector 200.

According to an embodiment, the controller 220 may control all operations of the communication interface 240 and the output interface 280 by executing the programs stored in the storage.

According to an embodiment, the communication interface 240 may communicate with components constituting the X-ray imaging system.

For example, the communication interface 240 may communicate with the X-ray imaging apparatus 100. In detail, the communication interface 240 may include a module for performing short-range communication such as NFC, RFID, and Bluetooth. The communication interface 240 may transmit ID information of the X-ray detector 200 to the X-ray imaging apparatus 100 via short-range communication such as NFC, RFID, and Bluetooth.

As another example, the communication interface 240 may communicate with the workstation 180. In detail, the communication interface 240 may transmit ID information of the X-ray detector 200 to the workstation 180. The communication interface 240 may also transmit information about X-rays detected by the X-ray detector 200 to the workstation 180. Furthermore, the communication interface 240 may receive a control signal that controls the X-ray detector 200 to be activated from the workstation 180. The communication interface 240 may also transmit unique information of the X-ray detector 200 to the workstation 180. The unique information of the X-ray detector 200 may include a serial number and IP address information of the X-ray detector 200 and other information composed of at least one of a letter and a numeral. Furthermore, the communication interface 240 may receive ID information of the X-ray detector 200 that is set by the workstation 180 from the workstation 180.

According to an embodiment, the communication interface 240 may communicate with an external device (e.g., the mobile device 330). For example, the communication interface 240 may transmit ID information of the X-ray detector 200 to the mobile device 330. As another example, the communication interface 240 may transmit information about a status of the X-ray detector 200 to the mobile device 330. Information about a status of the X-ray detector 200 may include pieces of information about a remaining battery capacity and an activation state of the X-ray detector 200, information about the number of X-ray images that are to be captured by the X-ray detector 200, and information about whether the X-ray detector 200 is currently transmitting an image to the workstation 180.

According to an embodiment, the output interface 280 may output ID information of the X-ray detector 200. For example, the output interface 280 may include an LED, other light-emitting devices, and an LCD for displaying ID information composed of letters or numerals. Furthermore, the output interface 280 may include a plurality of light sources.

According to an embodiment, the output interface 280 may output an optical signal. For example, the output interface 280 may output an optical signal of a color set by the workstation 180.

According to an embodiment, the output interface 280 may output information about a remaining battery capacity of the X-ray detector 200 by using the number of light sources from which optical signals are output among the plurality of light sources.

According to an embodiment, the output interface 280 may output information about communication sensitivity of the X-ray detector 200 by using an optical signal output from a light source. For example, the output interface 280 may output information about communication sensitivity of the X-ray detector 200 by using a blink period of an optical signal.

Figure 7:
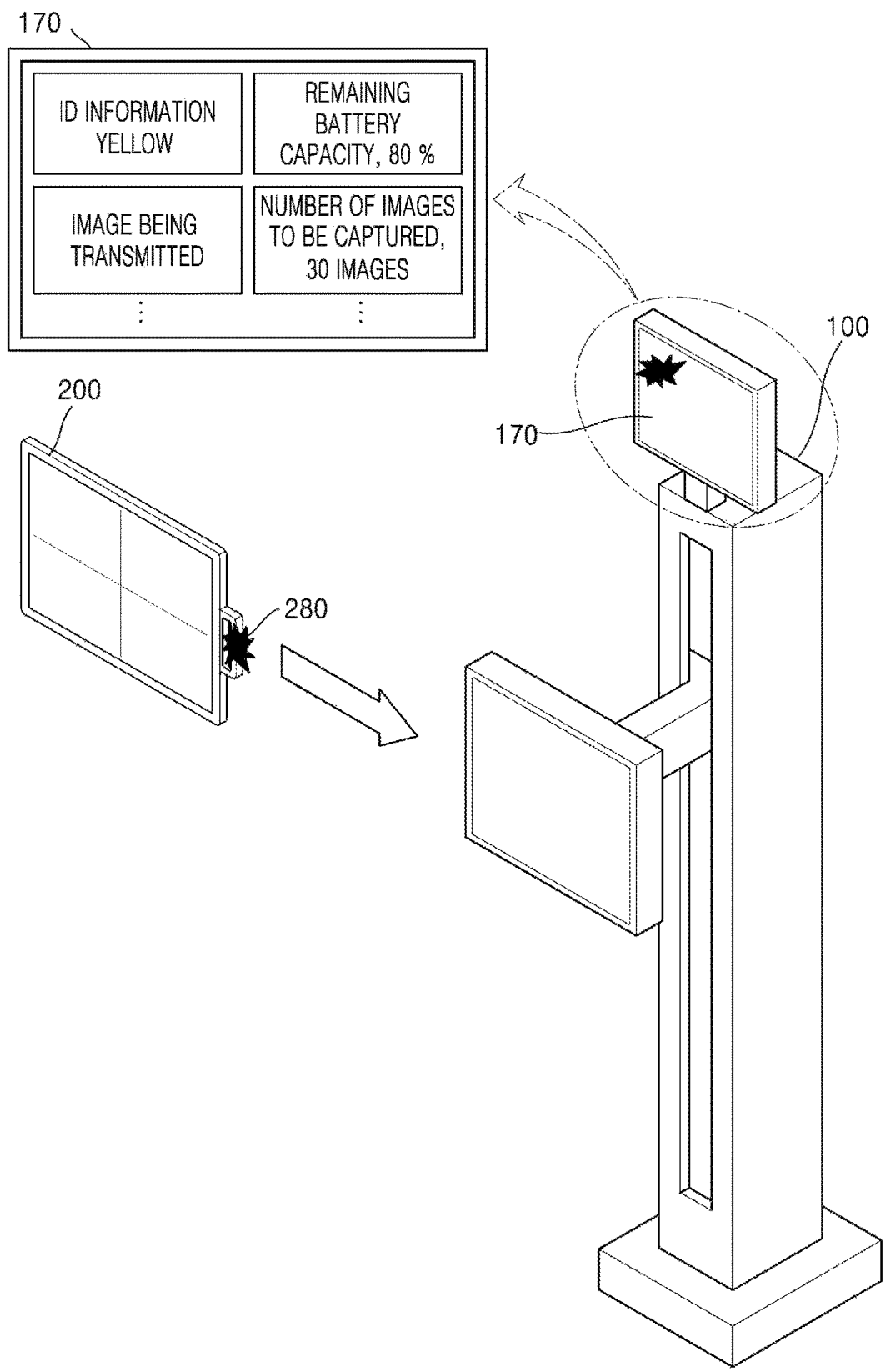
FIG. 7 illustrates an example of displaying information about an X-ray detector inserted into a receptor, according to an embodiment.

FIG. 7 illustrates an example of displaying information about the X-ray detector 200 inserted into the receptor 130, according to an embodiment.

Referring to FIG. 7, the X-ray detector 200 may output its own information. The X-ray imaging apparatus 100 may detect an optical signal output from the X-ray detector 200 that has been inserted into the receptor 130 of the X-ray imaging apparatus 100. The X-ray imaging apparatus 100 may then acquire ID information of the X-ray detector 200 based on the optical signal and output the acquired ID information.

According to an embodiment, the X-ray detector 200 may output its ID information as an optical signal of a color set by the workstation 180. When a plurality of X-ray detectors are registered with the X-ray imaging system, the workstation 180 may set colors respectively corresponding to the plurality of X-ray detectors as respective pieces of ID information of the plurality of X-ray detectors. For example, the workstation 180 may respectively set the pieces of ID information of the plurality of X-ray detectors to be red, orange, yellow, green, blue, indigo, and violet colors. An X-ray detector with its ID information set to a yellow color may output a yellow optical signal.

According to an embodiment, the X-ray detector 200 may output information about a remaining battery capacity thereof as an optical signal. For example, the X-ray detector 200 may output information about its remaining battery capacity by using the number of light sources from which optical signals are output among a plurality of light sources. As another example, the X-ray detector 200 may output information about its remaining battery capacity by using a blink period of an optical signal. In detail, when a blink period of an optical signal is less than a first threshold value, a remaining battery capacity of the X-ray detector 200 may be 80% When the blink period of the optical signal is greater than or equal to the first threshold value but is less than a second threshold value, the remaining battery capacity of the X-ray detector 200 may be 60%.

According to an embodiment, the X-ray detector 200 may output information about an activation state thereof as an optical signal. For example, the X-ray detector 200 may output information about an activation state thereof by using blinking of an optical signal. In detail, the X-ray detector 200 may indicate that it is in an activated state by outputting a non-blinking optical signal. The X-ray detector 200 may also indicate that it is in a standby state waiting for activation by outputting a blinking optical signal. The X-ray detector 200 may also indicate that it is transmitting a captured X-ray image by outputting a blinking optical signal. The X-ray detector 200 may also indicate that it is in a standby state waiting for a communication connection by outputting a blinking optical signal.

According to an embodiment, the X-ray detector 200 may output information about communication sensitivity thereof as an optical signal. For example, the output interface 280 may output information about communication sensitivity of the X-ray detector 200 by using a blink period of an optical signal. In detail, when a blink period of an optical signal is less than a first threshold value, the X-ray detector 200 may have high communication sensitivity. Otherwise, when the blink period of the optical signal is greater than or equal to the first threshold value but is less than a second threshold value, the X-ray detector 200 may have low communication sensitivity.

According to an embodiment, the X-ray imaging apparatus 100 may detect an optical signal output from the X-ray detector 200 inserted into the receptor 130 of the X-ray imaging apparatus 100. For example, the X-ray imaging apparatus 100 may detect a color of an optical signal output from the X-ray detector 200. As another example, the X-ray imaging apparatus 100 may detect a blink period of an optical signal output from the X-ray detector 200. As another example, the X-ray imaging apparatus 100 may detect the number of light sources from which optical signals are output among a plurality of light sources included in the X-ray detector 200.

According to an embodiment, the X-ray imaging apparatus 100 may acquire ID information of the X-ray detector 200 based on an optical signal. For example, the X-ray imaging apparatus 100 may acquire ID information of the X-ray detector 200 based on a color of an optical signal.

According to an embodiment, when acquiring the ID information of the X-ray detector 200, the X-ray imaging apparatus 100 may acquire information about a status of the X-ray detector 200 as well. For example, the X-ray imaging apparatus 100 may acquire at least one of pieces of information about a remaining battery capacity, an activation state, and communication sensitivity of the X-ray detector 200. Furthermore, the X-ray imaging apparatus 100 may acquire information about the number of X-ray images that are to be captured by the X-ray detector 200, based on information about a remaining battery capacity of the X-ray detector 200.

According to an embodiment, the X-ray imaging apparatus 100 may output the ID information of the X-ray detector 200. For example, the X-ray imaging apparatus 100 may output information about a color that has been set as the ID information of the X-ray detector 200. In detail, the X-ray imaging apparatus 100 may display ID information of the X-ray detector 200 that has been set to a yellow color as the word "Yellow". As another example, the X-ray imaging apparatus 100 may display ID information of the X-ray detector 200, which has been set to a yellow color, as a yellow image.

According to an embodiment, when the ID information of the X-ray detector 200 is output, the X-ray imaging apparatus 100 may also output information about whether the X-ray detector 200 has been inserted into the receptor 130 and position information of the X-ray detector 200 inserted into the receptor 130.

According to an embodiment, when the ID information of the X-ray detector 200 is output, the X-ray imaging apparatus 100 may also output information about a status of the X-ray detector 200. For example, the X-ray imaging apparatus 100 may output at least one of pieces of information about a remaining battery capacity, an activation state, and communication sensitivity of the X-ray detector 200. Furthermore, the X-ray imaging apparatus 100 may output information about the number of X-ray images that are to be captured by the X-ray detector 200.

Figure 8:
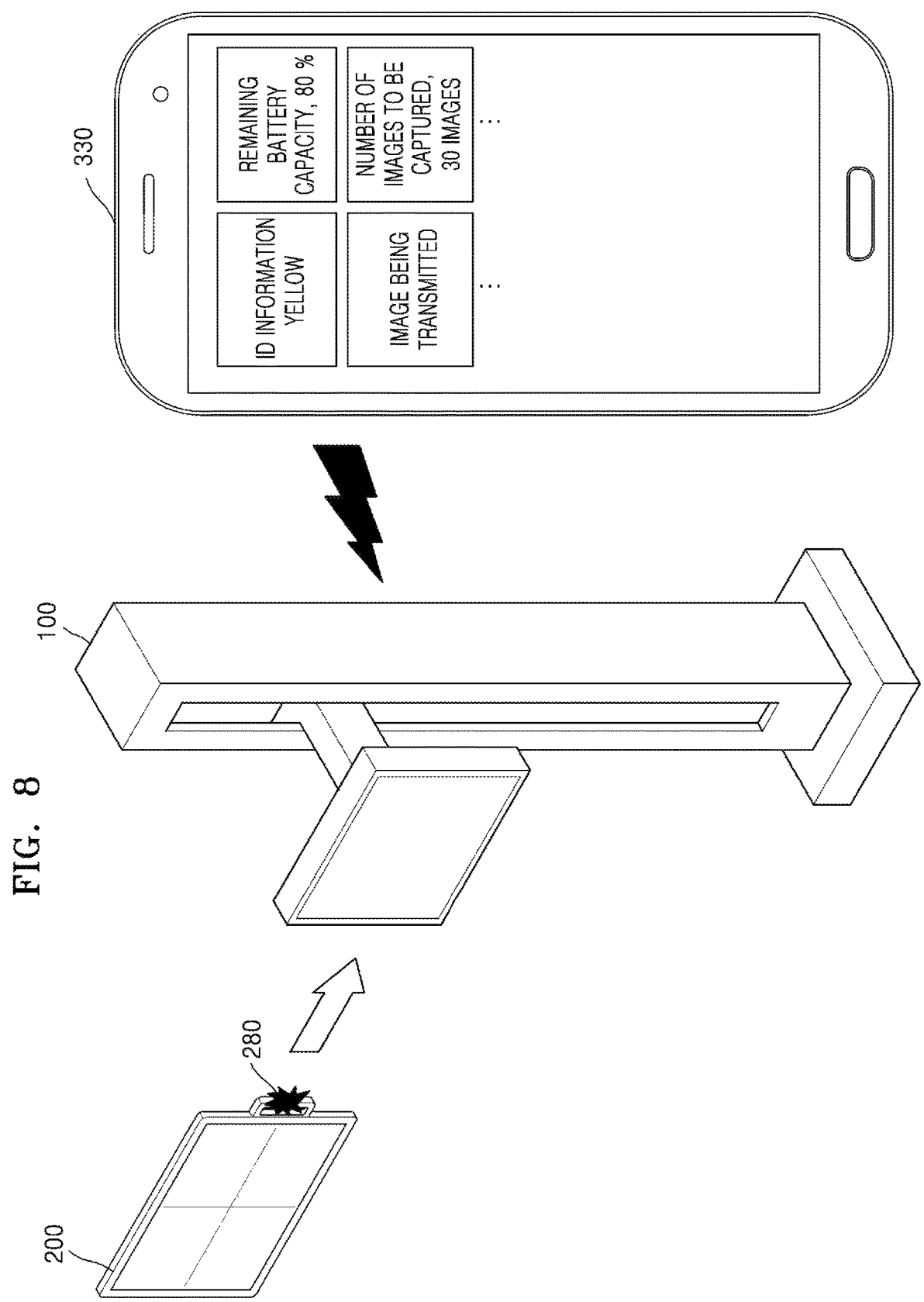
FIG. 8 illustrates an example of displaying information about an X-ray detector inserted into a receptor on a mobile device, according to an embodiment.

FIG. 8 illustrates an example of displaying information about the X-ray detector 200 inserted into the receptor 130 on the mobile device 330, according to an embodiment.

Referring to FIG. 8, the X-ray detector 200 may output its own ID information. The X-ray imaging apparatus 100 may detect an optical signal output from the X-ray detector 200 inserted into the receptor 130 of the X-ray imaging apparatus 100. The X-ray imaging apparatus 100 may acquire ID information of the X-ray detector 200 based on an optical signal. The X-ray imaging apparatus 100 may transmit the ID information to the mobile device 330, and the mobile device 330 may output the ID information.

Since a method by which the X-ray detector 200 outputs its information is similar to the method described with reference to FIG. 7, descriptions already provided above with respect to FIG. 7 will be omitted here.

Since a method by which the X-ray imaging apparatus 100 detects an optical signal output from the X-ray detector 200 inserted into the receptor 130 thereof is similar to the method described with reference to FIG. 7, descriptions already provided with respect to FIG. 7 will be omitted here.

Since a method by which the X-ray imaging apparatus 100 acquires ID information of the X-ray detector 200 based on an optical signal is similar to the method described with reference to FIG. 7, descriptions already provided with respect to FIG. 7 will be omitted here.

According to an embodiment, the X-ray imaging apparatus 100 may transmit ID information of the X-ray detector 200 to the mobile device 330. For example, the X-ray imaging apparatus 100 may transmit, to the mobile device 330, information about a color that is set as the ID information of the X-ray detector 200.

According to an embodiment, when the ID information is transmitted to the mobile device 330, the X-ray imaging apparatus 100 may also transmit, to the mobile device 330, at least one of information about whether the X-ray detector 200 has been inserted into the receptor 130 and position information of the X-ray detector 200 inserted into the receptor 130.

According to an embodiment, when the ID information is transmitted to the mobile device 330, the X-ray imaging apparatus 100 may also transmit information about a status of the X-ray detector 200 to the mobile device 330. For example, the X-ray imaging apparatus 100 may transmit, to the mobile device 330, at least one of pieces of information about a remaining battery capacity, an activation state, and communication sensitivity of the X-ray detector 200. Furthermore, the X-ray imaging apparatus 100 may transmit, to the mobile device 330, information about the number of X-ray images that are to be captured by the X-ray detector 200.

According to an embodiment, the mobile device 330 may output the received ID information of the X-ray detector 200 via a display included in the mobile device 330. Furthermore, the mobile device 330 may output the information about whether the X-ray detector 200 has been inserted into the receptor 130 and the position information of the X-ray detector 200 inserted into the receptor 130.

According to an embodiment, when the ID information of the X-ray detector 200 is output, the mobile device 330 may also output the information about the status of the X-ray detector 200. For example, the mobile device 330 may output at least one of pieces of information about a remaining battery capacity, an activation state, and communication sensitivity of the X-ray detector 200. Furthermore, the mobile device 330 may output information about the number of X-ray images that are to be captured by the X-ray detector 200.

Figure 9:
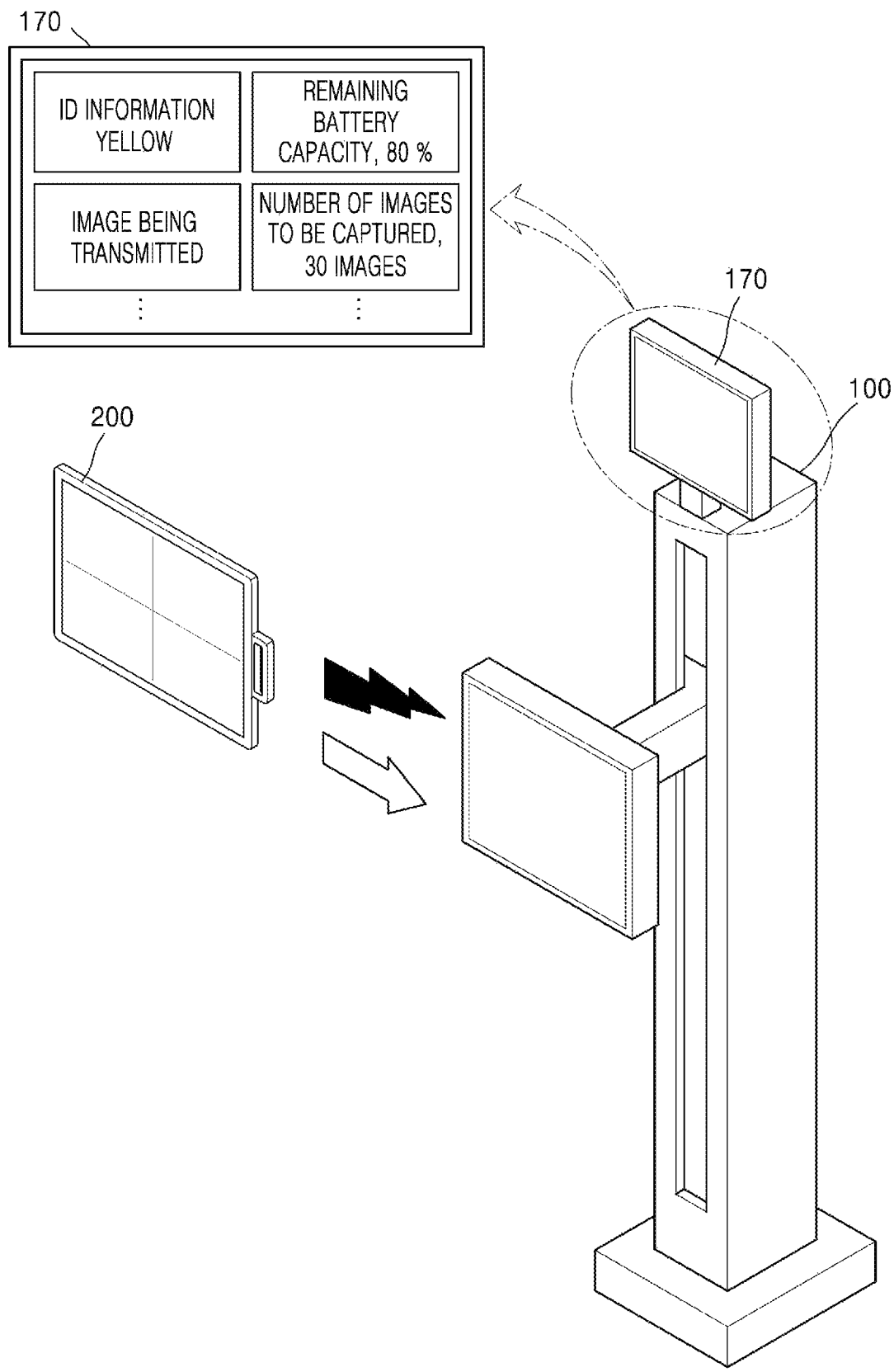
FIG. 9 is an example of displaying information about an X-ray detector inserted into a receptor, according to an embodiment.

FIG. 9 is an example of displaying information about the X-ray detector 200 inserted into the receptor 130, according to an embodiment.

Referring to FIG. 9, the X-ray detector 200 may output its information by transmitting the same to the X-ray imaging apparatus 100. The X-ray imaging apparatus 100 may acquire ID information of the X-ray detector 200 from the received information about the X-ray detector 200 and output the acquired ID information.

According to an embodiment, the X-ray detector 200 may output its information by transmitting the same to the X-ray imaging apparatus 100. The information about the X-ray detector 200 may include ID information of the X-ray detector 200 set by the workstation 180 and information about a status of the X-ray detector 200. The information about the status of the X-ray detector 200 may include pieces of information about a remaining battery capacity, an activation state, and communication sensitivity of the X-ray detector 200, information about the number of X-ray images that are to be captured by the X-ray detector 200, and information about whether the X-ray detector 200 is currently transmitting an image to the workstation 180.

According to an embodiment, ID information of the X-ray detector 200 may be composed of a letter, a numeral, or any combination thereof. For example, ID information of the X-ray detector 200 may be set to be S1, S2, S3, S4, T1, T2, T3, and T4.

According to an embodiment, the X-ray detector 200 may transmit information about the X-ray detector 200 to the X-ray imaging apparatus 100 over a short-range communication network created when the X-ray detector 200 is inserted into the receptor 130.

According to an embodiment, the X-ray imaging apparatus 100 may acquire ID information of the X-ray detector 200 from the received information about the X-ray detector 200. Furthermore, the X-ray imaging apparatus 100 may acquire information about a status of the X-ray detector 200 from the information about the X-ray detector 200.

According to an embodiment, the X-ray imaging apparatus 100 may output ID information of the X-ray detector 200. Since a method by which the X-ray imaging apparatus 100 outputs ID information is similar to the method described with reference to FIG. 7, descriptions already provided above with respect to FIG. 7 will be omitted here.

According to an embodiment, the X-ray imaging apparatus 100 may transmit information about a status of the X-ray detector 200 to the mobile device 330. The mobile device 330 may acquire at least one of the pieces of ID information and information about a status of the X-ray detector 200 from information about the X-ray detector 200. The mobile device 330 may output the ID information of the X-ray detector 200. Furthermore, the mobile device 330 may output information about whether the X-ray detector 200 has been inserted into the receptor 130 and position information of the X-ray detector 200 inserted into the receptor 130. In addition, the mobile device 330 may output the information about the status of the X-ray detector 200. Since a method by which the mobile device 330 outputs ID information is similar to the method described with reference to FIG. 8, descriptions already provided above with respect to FIG. 8 will be omitted here.

Figure 10:
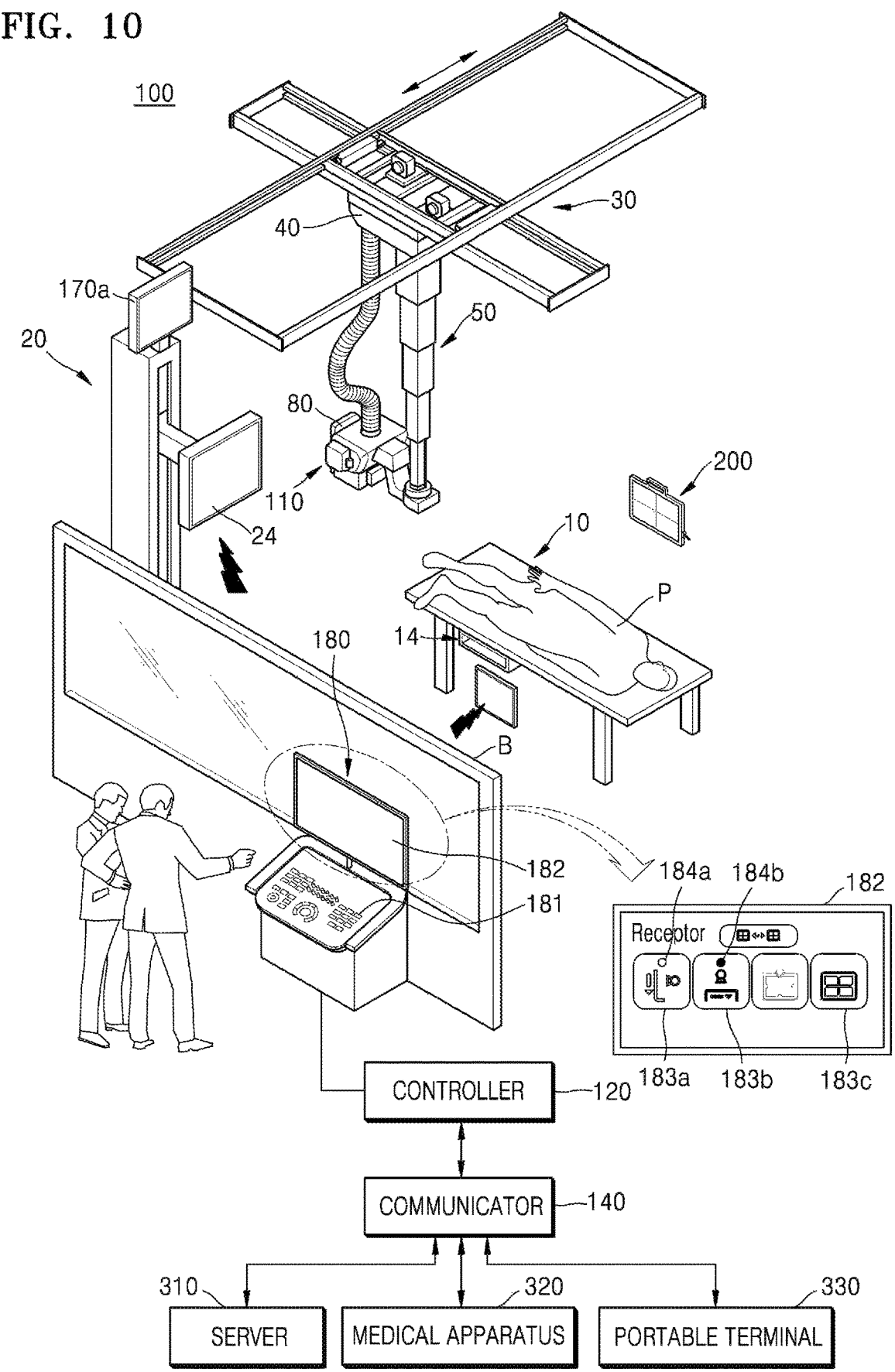
FIG. 10 is a diagram for explaining an operation of a workstation according to an embodiment.

FIG. 10 is a diagram for explaining an operation of a workstation 180 according to an embodiment.

The workstation 180 may control operations of an X-ray detector 200 and an X-ray imaging apparatus 100 included in an X-ray imaging system. A plurality of X-ray detectors and a plurality of X-ray imaging apparatuses may be included in the X-ray imaging system.

According to an embodiment, the workstation 180 may register a plurality of X-ray detectors with the X-ray imaging system. The workstation 180 may register the plurality of X-ray detectors based on pieces of unique information respectively received from the plurality of X-ray detectors. Unique information of the X-ray detector 200 may include a serial number and IP address information of the X-ray detector 200 and other information composed of at least one of a numeral and a letter.

According to an embodiment, when an X-ray detector is registered with the X-ray imaging system, the workstation 180 may set ID information with respect to the X-ray detector. The workstation 180 may respectively set pieces of ID information of the plurality of X-ray detectors to be respectively different colors. The workstation 180 may set pieces of ID information of the plurality of X-ray detectors to be respectively composed of different letters, numerals, or combinations thereof. The workstation 180 may transmit the pieces of ID information respectively set with respect to the plurality of X-ray detectors.

According to an embodiment, the workstation 180 may receive ID information and position information of the X-ray detector 200 inserted into a receptor of each of the plurality of X-ray imaging apparatuses. For example, position information of the X-ray detector 200 may include at least one of stand position information, table position information, and portable position information.

According to an embodiment, the workstation 180 may control the X-ray detector 200 to be activated. The workstation 180 may control the X-ray detector 200 to be activated based on ID information and position information of the X-ray detector 200 received from the X-ray imaging apparatus 100. The workstation 180 may control the X-ray detector 200 inserted into an X-ray imaging apparatus where an object to be imaged is placed, such that the X-ray detector 200 is activated.

According to an embodiment, the workstation 180 may control X-rays to be projected onto the activated X-ray detector 200 based on the received ID information and position information of the X-ray detector 200.

According to an embodiment, the workstation 180 may receive from the X-ray detector 200 information about X-rays detected by the X-ray detector 200. The workstation 180 may generate an X-ray image based on the information about X-rays.

According to an embodiment, a display 182 of the workstation 180 may display a list of the plurality of X-ray detectors registered with the X-ray imaging system on a user interface screen. For example, the workstation 180 may display, in the list of the plurality of X-ray detectors, at least one of unique information, ID information and position information of each of the plurality of X-ray detectors. As another example, the workstation 180 may display at least one of unique information, ID information, and position information of an X-ray detector selected from the list of the plurality of X-ray detectors.

According to an embodiment, the workstation 180 may display pieces of ID information 184a and 184b of X-ray detectors respectively inserted into receptors 14 and 24 of the plurality of X-ray imaging apparatuses. For example, the workstation 180 may display, on the display 182 included therein, X-ray detector icons 183a, 183b, and 183c among which the X-ray detector icons 183a and 183b respectively contain the pieces of ID information 184a and 184b. In detail, when ID information of an X-ray detector inserted into the receptor 24 of a stand type X-ray imaging apparatus 20 is set to a yellow color, the display 182 of the workstation 180 may output a yellow color as the ID information 184a of the X-ray detector included in the X-ray detector icon 183a indicating stand position information. When ID information of an X-ray detector inserted into the receptor 14 of a table type X-ray imaging apparatus 10 is set to a violet color, the display 182 of the workstation 180 may output a violet color as the ID information 184b of the X-ray detector included in the X-ray detector icon 183b.

According to an embodiment, the workstation 180 may receive an input of selecting one of the X-ray detector icons 183a, 183b, and 183c from the user. For example, the workstation 180 may receive from the user an input of selecting one of the X-ray detector icons 183a, 183b, and 183c respectively indicating stand position information, table position information, and portable position information.

According to an embodiment, the workstation 180 may control an X-ray detector corresponding to the selected X-ray detector icon 183a, 183b, or 183c to be activated. For example, when the user selects the X-ray detector icon 183a indicating stand position information, the workstation 180 may control the X-ray detector inserted into the receptor 24 of the stand type X-ray imaging apparatus 20 to be activated. When the user selects the X-ray detector icon 183b indicating table position information, the workstation 180 may control the X-ray detector inserted into the receptor 14 of the table type X-ray imaging apparatus 10 to be activated.

According to an embodiment, the workstation 180 may control an X-ray radiation device 110 to emit X-rays onto an activated X-ray detector. The workstation 180 may receive information about X-rays detected by the X-ray detector onto which the X-rays are projected. The workstation 180 may then generate an X-ray image based on the received information about X-rays.

According to an embodiment, the user may efficiently distinguish a plurality of X-ray detectors from one another and select the X-ray detector 200 to be used for imaging, based on the pieces of ID information 184a and 184b of X-ray detectors, which are displayed on the display 182 of the workstation 180, and pieces of ID information of X-ray detectors displayed on displays (e.g., 170a) of the plurality of X-ray imaging apparatuses.

Figure 11:
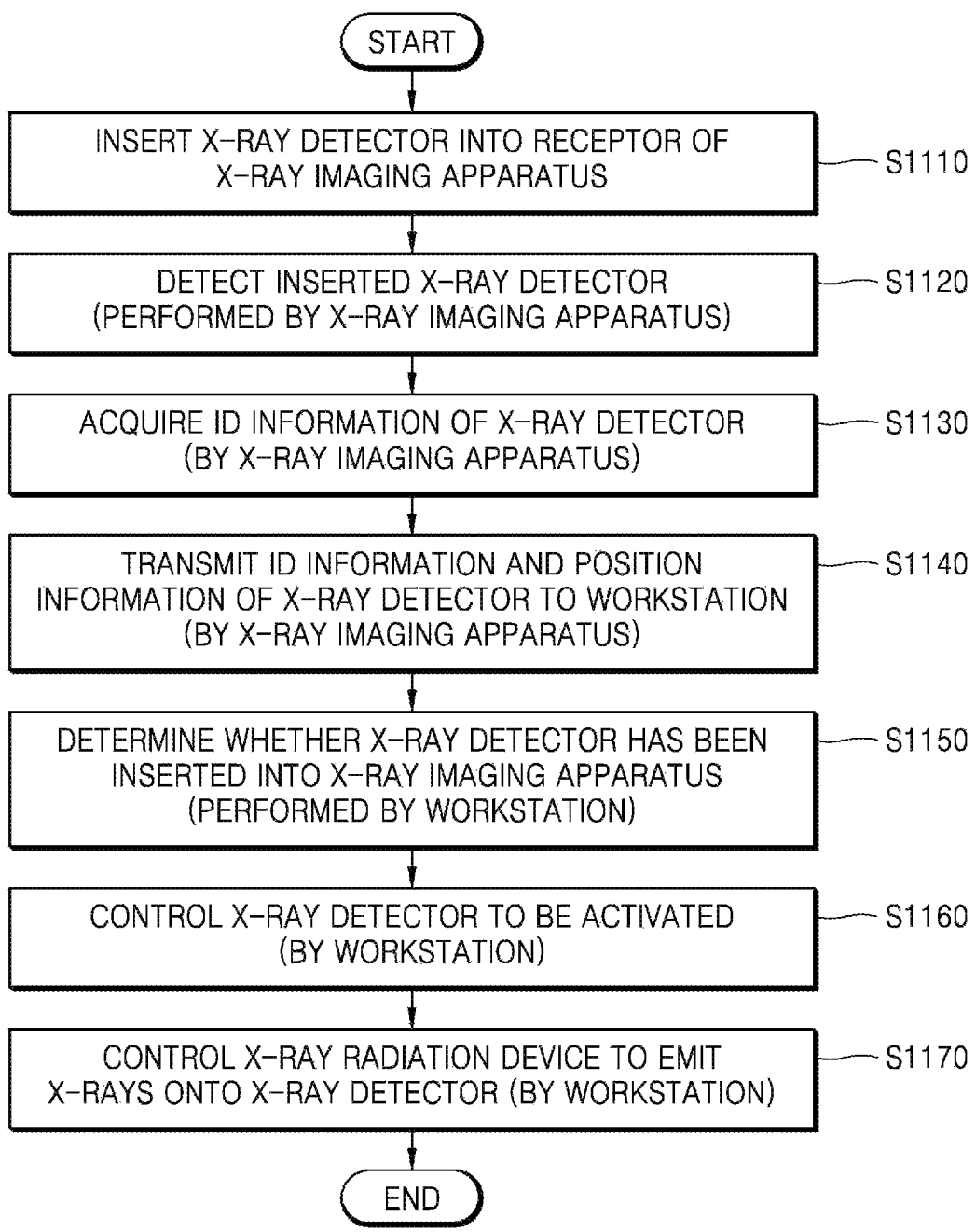
FIG. 11 is a flowchart illustrating an operation of a workstation according to an embodiment.

FIG. 11 is a flowchart illustrating an operation of the workstation 180 according to an embodiment.

The X-ray detector 200 may be inserted into one of the receptors 14 and 24 of the plurality of X-ray imaging apparatuses 10 and 20 included in the X-ray imaging system (S1110). According to an embodiment, ID information of the X-ray detector 200 may be set. Since ID information of the X-ray detector 200 has been described above, a detailed description thereof will be omitted here.

An X-ray imaging apparatus with the X-ray detector 200 inserted therein may detect the X-ray detector 200 (S1120). Descriptions are already provided above with respect to the method by which an X-ray imaging apparatus detects the X-ray detector 200, and thus, will not be repeated below.

The X-ray imaging apparatus may acquire ID information of the inserted X-ray detector 200 (S1130). Descriptions are already provided above with respect to the method by which the X-ray imaging apparatus acquires ID information of the X-ray detector 200, and thus, will not be repeated below.

The X-ray imaging apparatus may transmit the ID information and position information of the X-ray detector 200 to the workstation 180 (S1140). Descriptions are already provided above with respect to the method by which an X-ray imaging apparatus generates position information of the X-ray detector 200, and thus, will not be repeated below.

The workstation 180 may determine whether the X-ray detector 200 has been inserted into the X-ray imaging apparatus (S1150). The workstation 180 may determine whether the X-ray detector 200 has been registered with the X-ray imaging system based on the ID information of the X-ray detector 200 received from the X-ray imaging apparatus. Furthermore, when ID information of the X-ray detector 200 registered with the X-ray imaging system is identical to the received ID information of the X-ray detector 200, the workstation 180 may determine an X-ray imaging apparatus into which the X-ray detector 200 has been inserted, based on the position information of the X-ray detector 200. The workstation 180 may display ID information of the X-ray detector 200 inserted into the X-ray imaging apparatus on the display 182. Since the method by which the workstation 180 displays ID information of an X-ray detector has been described with reference to FIG. 10, a detailed description thereof will be omitted here.

The workstation 180 may control the X-ray detector 200 to be activated (S1160). According to an embodiment, the workstation 180 may receive an input of selecting one of the X-ray detector ions 183a, 183b, and 183c from the user. The workstation 180 may control an X-ray detector corresponding to the selected X-ray detector icon 183a, 183b, or 183c such that the X-ray detector is activated. Since the method of activating the X-ray detector 200 has been described with reference to FIG. 10, a detailed description thereof will be omitted here.

The workstation 180 may control the X-ray radiation device 100 to emit X-rays onto the activated X-ray detector 200 (S1170).

According to an embodiment, the user may control X-rays to be emitted toward an X-ray imaging apparatus where an object P is placed, thereby preventing emission of unnecessary X-rays onto the object P.

Figure 12:
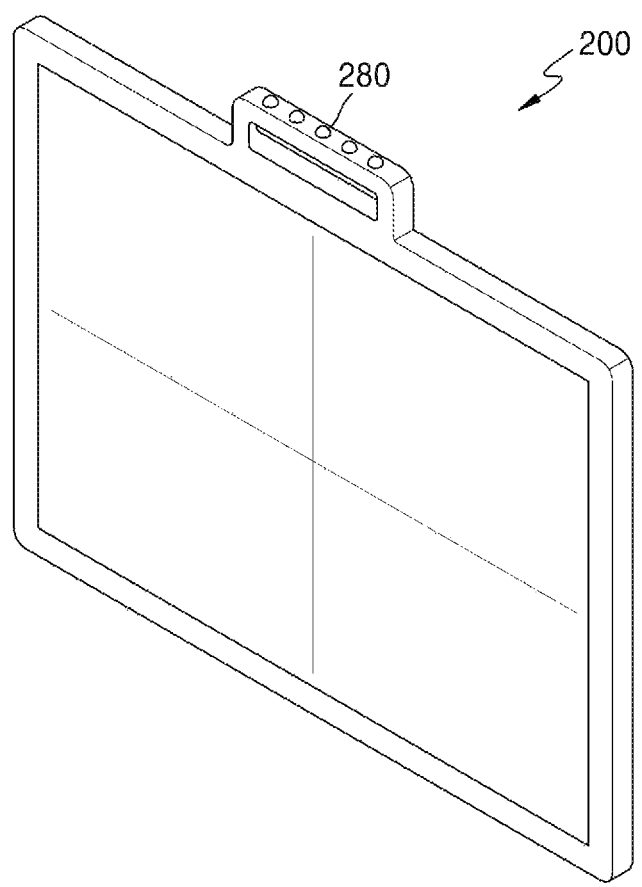
FIG. 12 illustrates an example of displaying information about an X-ray detector on an outer surface of the X-ray detector.

FIG. 12 illustrates an example of displaying information about an X-ray detector 200 on an outer surface of the X-ray detector 200.

Referring to FIG. 12, the X-ray detector 200 may have a plurality of light sources 280 on an outer surface thereof.

According to an embodiment, each of the plurality of light sources 280 may be composed of at least one of an LCD, an LED, and other light-emitting devices that output an optical signal.

According to an embodiment, the plurality of light sources 280 may respectively output optical signals of different colors.

According to an embodiment, the X-ray detector 200 may display a remaining battery capacity of the X-ray detector 200 by using the number of light sources from which optical signals are output among the plurality of light sources. For example, the X-ray detector 200 may have five (5) light sources on its outer surface. When all of the five light sources in the X-ray detector 200 respectively output optical signals, a remaining battery capacity of the X-ray detector 200 may be 80% to 100%. When four of the light sources in the X-ray detector 200 output optical signals, the remaining battery capacity of the X-ray detector 200 may be 60% to 80%. When three of the light sources in the X-ray detector 200 output optical signals, the remaining battery capacity of the X-ray detector 200 may be 40% to 60%. When two of the light sources in the X-ray detector 200 output optical signals, the remaining battery capacity of the X-ray detector 200 may be 20% to 40%. When one of the light sources in the X-ray detector 200 outputs an optical signal, the remaining battery capacity of the X-ray detector 200 may be 1% to 20%.

Embodiments may be implemented through computer-readable recording media having stored thereon computer-executable instructions and data. The instructions may be stored in the form of program code, and when executed by a processor, generate a predetermined program module to perform a specific operation. Furthermore, when being executed by the processor, the instructions may perform specific operations according to the embodiments.

According to embodiments, a user of an X-ray imaging system including a plurality of X-ray imaging apparatuses may easily identify the X-ray imaging apparatus 100 into which the X-ray detector has been inserted. Furthermore, the user may easily activate the X-ray detector 200 inserted into the X-ray imaging apparatus 100 where an object P is placed. Then, the user may control X-rays to be emitted toward the X-ray imaging apparatus 100 where the object P is placed, thereby preventing emission of unnecessary X-rays onto the object P.

An X-ray imaging apparatus according to an embodiment may be implemented by mounting the X-ray detector 200 sensing interface (e.g., an optical sensor) and a display to an X-ray imaging apparatus of the related art. In other words, even without buying a new X-ray imaging apparatus, the user of an X-ray imaging system including a plurality of X-ray imaging apparatuses may easily identify the X-ray imaging apparatus into which the X-ray detector 200 has been inserted.

While one or more embodiments have been described with reference to the figures, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

The invention claimed is:

1. An X-ray imaging apparatus comprising:
an X-ray radiation device configured to emit X-rays;
a receptor into which a first X-ray detector configured to detect the emitted X-rays is inserted;
an X-ray detector sensing interface configured to detect whether the first X-ray detector has been inserted into the receptor, acquire first identification information of the first X-ray detector inserted into the receptor, and generate first position information indicating that the first X-ray detector has been inserted into the receptor;
an output interface configured to output information about the first X-ray detector; and
a controller configured to control the output interface to output the first position information and the first identification information,
wherein the first identification information is identification information set by a workstation of an X-ray imaging system including the X-ray imaging apparatus,
wherein the first X-ray detector is further configured to output an optical signal corresponding to the first identification information,
wherein the X-ray detector sensing interface comprises an optical sensor configured to detect the optical signal, and
wherein the controller is further configured to acquire the first identification information based on the detected optical signal.

2. The X-ray imaging apparatus of claim 1, wherein the controller is further configured to:
acquire the first identification information corresponding to a color of the optical signal; and
control the output interface to output the acquired first identification information as information about the color of the optical signal.

3. The X-ray imaging apparatus of claim 1, wherein the first X-ray detector comprises a plurality of light sources configured to respectively output optical signals,
wherein the optical sensor is further configured to detect a number of light sources from which optical signals are output from among the plurality of light sources in the first X-ray detector, and
wherein the controller is further configured to:
acquire information about a remaining battery capacity of the first X-ray detector based on the detected number of light sources; and
control the output interface to further output the information about the remaining battery capacity of the first X-ray detector.

4. The X-ray imaging apparatus of claim 1, wherein the output interface comprises a communication interface configured to transmit the first identification information to a mobile device comprising a display.

5. The X-ray imaging apparatus of claim 1, wherein the X-ray detector sensing interface is further configured to acquire information about a status of the first X-ray detector via short-range communication, and
wherein the controller is further configured to control the output interface to output the information about the status of the first X-ray detector.

6. A method of controlling an X-ray imaging apparatus, the method comprising:
detecting whether a first X-ray detector has been inserted into a receptor;
acquiring first identification information of the first X-ray detector inserted into the receptor from the first X-ray detector;
generating first position information indicating that the first X-ray detector has been inserted into the receptor; and
outputting the first position information and the first identification information, wherein the first identification information is identification information set by a workstation of an X-ray imaging system including the X-ray imaging apparatus, wherein the detecting of the first X-ray detector comprises outputting an optical signal corresponding to the first identification information generated by an output interface of the first X-ray detector, and wherein the acquiring of the first identification information comprises acquiring the first identification information based on the detected optical signal.

7. The method of claim 6, wherein the acquiring of the first identification information comprises acquiring the first identification information corresponding to a color of the optical signal, and wherein the outputting of the first identification information comprises outputting the first identification information as information about the color of the optical signal.

8. The method of claim 6, wherein the detecting of the first X-ray detector comprises detecting a number of light sources from which optical signals are output, from among a plurality of light sources included in the first X-ray detector and configured to respectively output optical signals, wherein the acquiring of the first identification information comprises acquiring information about a remaining battery capacity of the first X-ray detector based on the detected number of light sources, and wherein the outputting of the first identification information comprises outputting the information about the remaining battery capacity of the first X-ray detector.

9. The method of claim 6, further comprising transmitting the first identification information to a mobile device.

10. The method of claim 6, wherein the acquiring of the first identification information comprises acquiring information about a status of the first X-ray detector from the first X-ray detector, and wherein the outputting of the first identification information comprises outputting the information about the status of the first X-ray detector.

11. The method of claim 6, further comprising:

transmitting, to the workstation, the first identification information and the first position information indicating that the first X-ray detector has been inserted into the receptor of the X-ray imaging apparatus, wherein the transmitting is performed by the X-ray imaging apparatus;

controlling the first X-ray detector to be activated based on the first identification information and the first position information, wherein the controlling is performed by the workstation; and controlling X-rays to be emitted toward the activated first X-ray detector, wherein the controlling is performed by the workstation.

12. The method of claim 11, further comprising:

setting different pieces of identification information respectively with respect to a plurality of X-ray detectors, wherein the setting is performed by the workstation; and outputting an optical signal of a color corresponding to identification information of the first X-ray detector, wherein the outputting is performed by the first X-ray detector.

13. A computer program product comprising a computer-readable storage medium, the computer readable storage medium comprising instructions for detecting whether a first X-ray detector has been inserted into a receptor;

acquiring first identification information of the first X-ray detector inserted into the receptor from the first X-ray detector;

generating first position information indicating that the first X-ray detector has been inserted into the receptor; and outputting the first position information and the first identification information, wherein the first identification information is identification information set by a workstation of an X-ray imaging system including an X-ray imaging apparatus, wherein the detecting of the first X-ray detector comprises outputting an optical signal corresponding to the first identification information generated by an output interface of the first X-ray detector, and wherein the acquiring of the first identification information comprises acquiring the first identification information based on the detected optical signal.

* * * * *